United States Patent [19]
McLaughlin et al.

[11] Patent Number: 5,483,976
[45] Date of Patent: Jan. 16, 1996

[54] MECHANICALLY ACTUATED URETHRAL PLUG ASSEMBLY AND METHOD FOR CONTROLLING URINARY INCONTINENCE

[75] Inventors: Paul D. McLaughlin, Scituate; Sharad Joshi, Watertown; Azhar Syad; John Simon, both of Boston, all of Mass.

[73] Assignee: UroMed Corporation, Watertown, Mass.

[21] Appl. No.: 62,592

[22] Filed: May 17, 1993

Related U.S. Application Data

[63] Continuation-in-part of Ser. No. 811,571, Dec. 20, 1991, which is a continuation-in-part of Ser. No. 746,364, Aug. 16, 1991, abandoned, which is a continuation-in-part of Ser. No. 636,285, Dec. 31, 1990, Pat. No. 5,090,424.

[51] Int. Cl.⁶ .................................. A61F 5/48; A61F 2/00
[52] U.S. Cl. .................................. 128/885; 128/DIG. 25; 600/29
[58] Field of Search ........................ 128/885, 886, 128/DIG. 25; 600/29, 30, 31

[56] References Cited

U.S. PATENT DOCUMENTS

| | | | |
|---|---|---|---|
| 2,533,924 | 12/1950 | Foley | 128/885 |
| 2,638,093 | 5/1953 | Kulick . | |
| 3,789,828 | 2/1974 | Schulte . | |
| 3,797,478 | 3/1974 | Walsh et al. . | |
| 3,841,304 | 10/1974 | Jones . | |
| 4,019,499 | 4/1977 | Fitzgerald . | |
| 4,457,299 | 7/1984 | Cornwell . | |
| 4,553,533 | 11/1985 | Leighton . | |
| 4,682,592 | 7/1987 | Thoregard | 128/303 R |
| 4,800,900 | 1/1989 | French | 128/885 |
| 4,846,784 | 7/1989 | Haber | 128/DIG. 25 |
| 4,850,963 | 7/1989 | Sparks et al. | 600/29 |
| 4,938,759 | 7/1990 | Enscore et al. | 604/896.1 |
| 4,946,449 | 8/1990 | Davis, Jr. | 604/256 |
| 4,950,223 | 8/1990 | Silvanov | 128/DIG. 25 |
| 5,090,424 | 2/1992 | Simon et al. | 128/885 |
| 5,114,380 | 5/1992 | Larsen | 452/176 |
| 5,114,398 | 5/1992 | Trick et al. | 604/29 |
| 5,116,387 | 5/1992 | Berg | 623/66 |

FOREIGN PATENT DOCUMENTS

| | | |
|---|---|---|
| 8810106 | 12/1988 | WIPO . |
| 8900030 | 1/1989 | WIPO . |

OTHER PUBLICATIONS

Nielsen et al., "The Urethral Plug: A New Treatment Modality for Genuine Urinary Stress Incontinence in Women", Nov. 1990, pp. 1199–1202 Journal of Urology, vol. 144..

*Primary Examiner*—Michael A. Brown
*Attorney, Agent, or Firm*—Lorusso & Loud

[57] ABSTRACT

A urethral plug assembly having a cooperating housing and inner member, the plug assembly possessing a contracted diameter for insertion and removal through the orifice of the urethra, and a larger, expanded diameter for blocking the flow of urine in the urethra, bladder neck and bladder. A larger diameter is achieved by mechanical deployment of the inner member, which results in the expansion of the housing, or in another embodiment, which results in the expansion of the inner member. A balloon is additionally expanded, thus sealing the plug assembly to the urethral, bladder neck and bladder wall. The plug assembly further has a meatal plate for anchoring the plug assembly in the urethra, preventing migration of the plug assembly into the bladder. Removal of the plug assembly for bladder evacuation, is easily accomplished by pulling a cord causing the contraction of the expanded housing or inner member, and grasping a tab associated with said meatal plate. In accordance with a further feature of the invention, there is provided a method for controlling incontinence in humans.

37 Claims, 5 Drawing Sheets

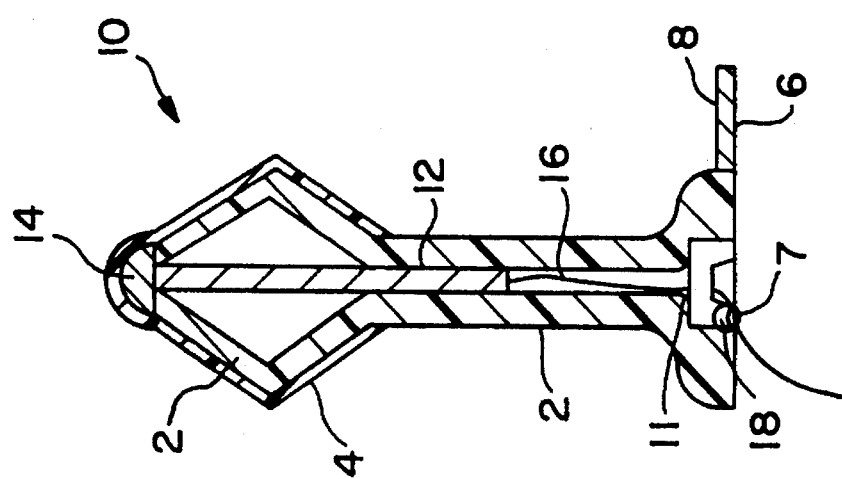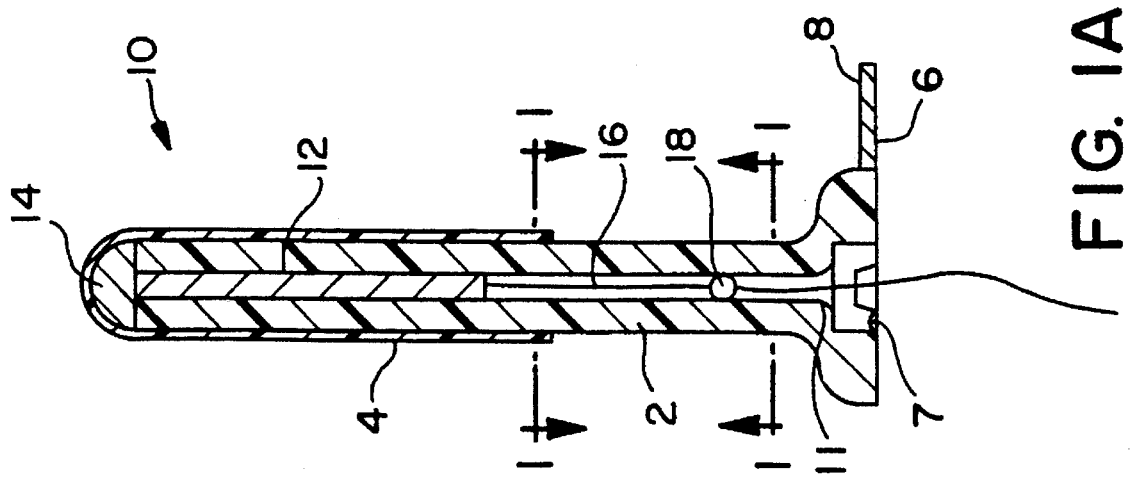

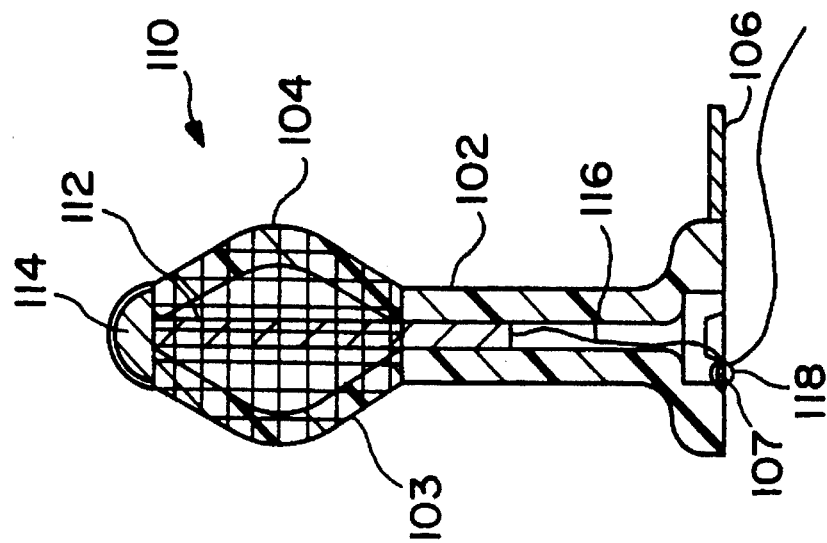
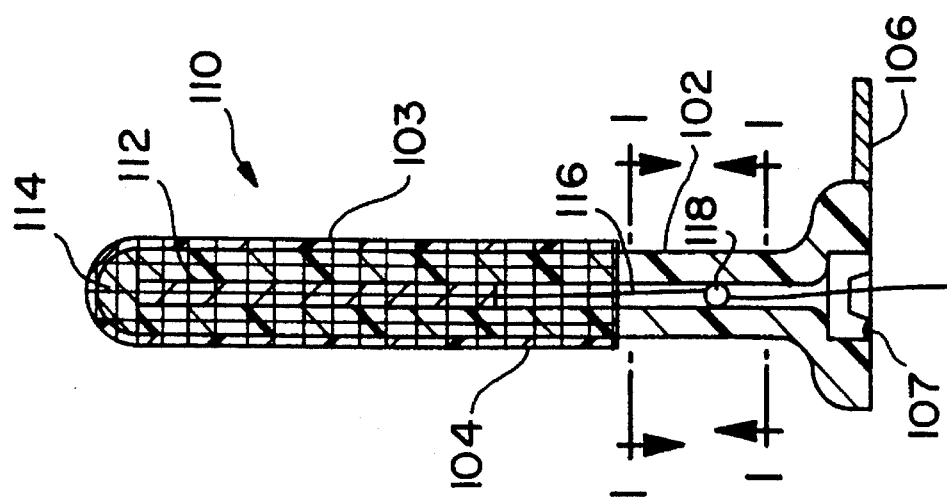
FIG. 2B
FIG. 2A

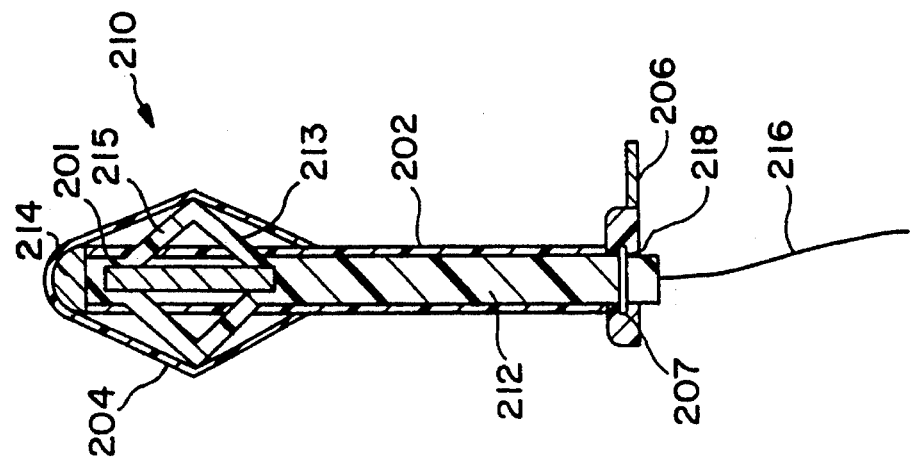
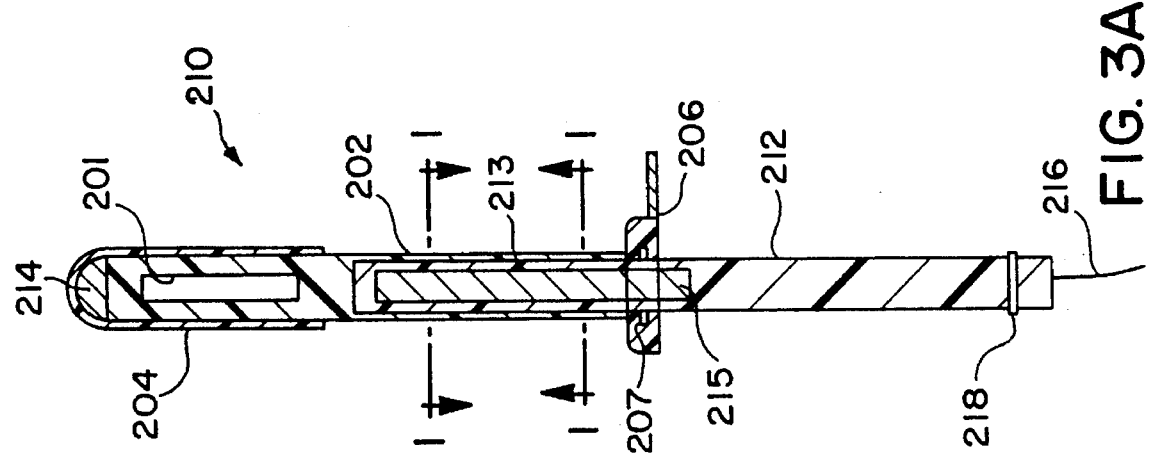
FIG. 3B
FIG. 3A

MECHANICALLY ACTUATED URETHRAL PLUG ASSEMBLY AND METHOD FOR CONTROLLING URINARY INCONTINENCE

This is a continuation-in-part of application(s) Ser. No. 07/811,571 filed on Dec. 20, 1991 which is CIP of U.S. Ser. No. 746,364 filed Aug. 16, 1991 now abandoned, which is a CIP of U.S. Ser. No. 636,285 filed Dec. 31, 1990 (now U.S. Pat. No. 5,090,424).

BACKGROUND OF THE INVENTION

FIELD OF THE INVENTION

The present invention relates to a novel plug assembly which is inserted into the urethra to control urinary incontinence.

DEFINITIONS

"Mechanical" or "mechanically" is defined as that which operates by the motion of social elements.

"Rod is defined as a solid member, a tubular member, or a string.

DESCRIPTION OF THE PRIOR ART

Urinary stress incontinence is defined as the involuntary loss of urine when the pressure within the urethra exceeds the maximum urethral pressure required for maintaining closure. While the problem of urinary incontinence occurs in men and women, it is an affliction especially common in women of child bearing age and beyond.

There are in existence many methods used to address the problem of incontinence. Bladder neck suspension surgery, wherein the neck of the bladder is reduced by suspending the bladder, is perhaps the most desirable way to treat incontinence, especially in younger patients. However, there are numerous risks associated with such surgery, notwithstanding the expense. For some patients, surgery is not recommended for medical or other reasons, and for those with mild incontinence surgery is not an appropriate solution.

Also in existence are a variety of devices for controlling urinary incontinence. Many of these devices require surgery for implantation, and of these surgically implanted devices, there are two distinct types: non-manipulable devices and manipulable devices. One such non-manipulable device, described in U.S. Pat. No. 4,019,499, is a capsule filled with a variable amount of fluid. The capsule is surgically implanted between supporting tissue and the urethra to exert an occluding force thereon. A similar, non-manipulable capsule implant is described in U.S. Pat. No. 3,789,828. However, this device has ties extending therefrom to aid in fiber ingrowth, thus providing mechanical stability to the capsule. One problem associated with this device is the risk of fluid leakage. In addition to problems with leakage, severe tissue damage may result from the unnatural method in which such devices regulate incontinence.

Other surgically implanted devices exist which are manipulable. These devices provide the wearer with the ability to selectively control the operation of the device via manually operable elements implanted in the tissue surrounding the urethra. U.S. Pat. No. 4,428,365, and U.S. Pat. No. 4,846,784 each disclose an indwelling device having an inflatable chamber with an attached tubing and an inflation bulb. The wearer may manually adjust the pressure exhibited by the inflatable member on the urethra, simply by squeezing the tissue encasing the bulb. These devices, however, often produce thickening and scarring of surrounding tissue, making their usefulness questionable. Additional adverse effects associated with surgically implanted indwelling devices, whether non-manipulable or manipulable in nature, are encrustation, irritation and infection.

There are also known in the art certain indwelling devices that do not require surgical implantation. These devices are inserted by a physician through the urethral orifice and allow the wearer to void either past or through the device. An example of such a device is disclosed in U.S. Pat. No. 4,850,963 in which a physician inserts a bolus of ferromagnetic material through the urethra and into the bladder. The bolus rests at the juncture of the bladder and urethra and is moved for bladder evacuation, by the relative positioning of a magnet across the body of the wearer. However, the bolus may become lodged in an area beyond the reaches of the magnetic force exhibited by the magnet, making the device inoperative. Another example of this type of indwelling device is the prestressed capsule disclosed in U.S. Pat. No. 4,457,299. The capsule is inserted by a physician within the lower interior of the urethra and is set at a prestressed pressure slightly above involuntary pressure. When the urine pressure exceeds the preset pressure of the capsule, the capsule deforms allowing urine to flow around the device. This device, however, has no feature to prevent migration of the device into the bladder. In U.S. Pat. No. 4,553,533 there is shown a prosthetic urethral sphincter valve which is placed in the urethra and anchored in the bladder. The patient increases his bladder pressure by means of a valsalva maneuver, and holds this pressure while the valve activates. Urine may then pass through the valve with the valve later returning to its closed position. This device is very complicated, expensive, difficult to manufacture and uncomfortable. Another physician-inserted device is disclosed in U.S. Pat. No. 3,797,478. This device has an expandable collar which is inflated after insertion, by an injection of fluid therein. When it is desired to remove the device, the inflated collar is ruptured or serrated, thus expelling the fluid into the wearer's body. Notwithstanding the cumbrous use of this device, there is a risk of infection associated with the release of injection fluid upon removal. Similarly, U.S. Pat. No. 3,841,304 discloses a plug which is inserted by a physician into the urethra and subsequently inflated to block the flow of urine. This device may be left in the body for extended periods. After insertion, the device merely requires repositioning in the urethra to permit bladder evacuation. Such a device leaves the wearer susceptible to infection, as bacteria may be introduced into the urethra during repositioning, or during indwelling time. Also, serious complications can occur upon removal, when a separate wire must be inserted therein. These devices being indwelling, are often cumbersome to the wearer and often cause numerous complications such as encrustation, irritation and infection.

Also known in the art are devices capable of being inserted by the wearer into the urethra. Such devices are removed for voiding, and then reintroduced into the urethra upon completion of bladder evacuation. An example of such a device is the solid-type urethral plug, described by Neilsen, Kurt K. et al., in "The Urethral Plug: A New Treatment Modality for Genuine Urinary Stress Incontinence in Women" J. Urology, vol. 44, p. 1100 (1990). This device consists of one or two solid spheres located along a soft shaft, and a thin, soft plate located at the end of the shaft. One sphere is located upstream of the maximum urethral closing pressure point, corresponding to the location of the sphincter. In the two sphere embodiment, the second sphere is located with its midpoint at the bladder neck, and is used to assist in reducing urinary flow and pressure transmission to the urethra so that the sphincter can operate. When the patient wants to evacuate the bladder, the plug is removed, evacuation occurs, and a fresh plug is inserted. One problem associated with this device is that the patient must have three urethral closure pressure profiles performed as well as other examinations, before the device is made for the wearer. Additional problems associated with this device include placement difficulties, lack of sealing capabilities associated therewith, inadequate retention thereby allowing expelling and inadequate anchoring by the plate at the meatus. In addition to such problems, is the discomfort associated with insertion and removal, due to the size profile and rigidity of the spheres, which maintain a constant diameter during insertion, and removal. Another "remove-to-void" device is disclosed in U.S. Pat. No. 5,090,424, which comprises a conformable urethral plug. The body of the plug forms a cavity which is in fluid communication with another cavity via a check-valve. Thus, fluid may be pumped into the cavity within the urethra to provide a custom fit. This device, like many others relying on liquids or gels for expansion, relies heavily on a fluid-tight valve in order to maintain retention. Should valve failure occur, evacuation would immediately follow. There is also a chance of fluid leakage into the body of the wearer should rupture of the plug occur.

In view of the above problems associated with the prior art, an easily manipulable device of a non-fluid construction, which is mechanically actuated, would be desirable to those afflicted with urinary incontinence.

SUMMARY OF THE INVENTION

One object of the invention is to provide a urethral plug assembly which is easily manipulated by the wearer.

Another object of the invention is improve the degree of comfort associated with insertion and removal of a urethral plug assembly.

A further object of the invention is to enhance the sealing ability of a urethral plug assembly with the urethral, bladder neck, or bladder wall.

Another object of the invention is to stabilize the placement of a urethral plug assembly at the urethral meatus, such that migration into the bladder will not occur.

Another object of the invention is to avoid the use of fluid for achieving the blockage of urine.

Another object of the invention is to reduce the risk of contamination to the wearer of a urethral plug assembly.

Still another object of the invention is to provide a method for controlling incontinence.

These and other objects of the invention are carried out by a novel urethral plug assembly comprising a cooperating housing and inner member, lying in coaxial engagement and possessing a contracted diameter for insertion and removal through the orifice of the urethra, and a larger, expanded diameter for blocking the flow of urine in the urethra, bladder neck and bladder. A larger diameter is achieved by mechanical deployment of the inner member resulting in the changing of the shape of the housing, or in another embodiment, the changing of the shape of the inner member. In each embodiment, this change in shape causes a balloon to expand, which seals the plug assembly to the urethral, bladder neck and bladder wall. The plug assembly further has a meatal plate for anchoring the plug assembly in the urethra. Removal of the plug assembly for bladder evacuation, is easily accomplished by pulling a cord causing the contraction of the inner member, and grasping a tab associated with said meatal plate. The meatal plate further serves to prevent migration of both the plug assembly and the cord into the bladder. In accordance with a further feature of the invention, there is provided a method for controlling incontinence in humans.

BRIEF DESCRIPTION OF THE DRAWINGS

FIG. 1A shows a first embodiment of the urethral plug assembly which has an expansible outer tube, in its contracted configuration.

FIG. 1B shows the first embodiment of the urethral plug assembly in its expanded configuration.

FIG. 2A shows a second embodiment of the urethral plug assembly which has a braided mesh, in its contracted configuration.

FIG. 2B shows the second embodiment of the urethral plug assembly in its expanded configuration.

FIG. 3A shows a third embodiment of the urethral plug assembly in its contracted configuration.

FIG. 3B shows the third embodiment of the urethral plug assembly in its expanded configuration.

DETAILED DESCRIPTION OF THE INVENTION

FIG. 1A shows the urethral plug assembly of the first embodiment 10, in its contracted configuration. The plug housing comprises a hollow, cylindrical tube 2 which is sized to be easily inserted through the orifice of the urethra. The tube 2 is made from a biocompatible material having characteristics of compressibility. Attached on the periphery thereof either by thermal bonding, laminating or other means, is a sealing membrane, or balloon, 4 which is adapted to rest against the outer tube 2. At the distal end of the tube 2 is a meatal plate 6. The meatal plate 6 is adapted to anchor the urethral plug assembly 10 at the meatus urinarius. To carry out this function of anchoring, the meatal plate 6 is of a thickness sufficient to withstand bodily compression during wear, preferably on the order of 1 millimeter or greater. The meatal plate 6 prevents the plug assembly 10 from passing through the orifice in the urethra ultimately leading into the bladder neck or bladder.

Figure 4B:
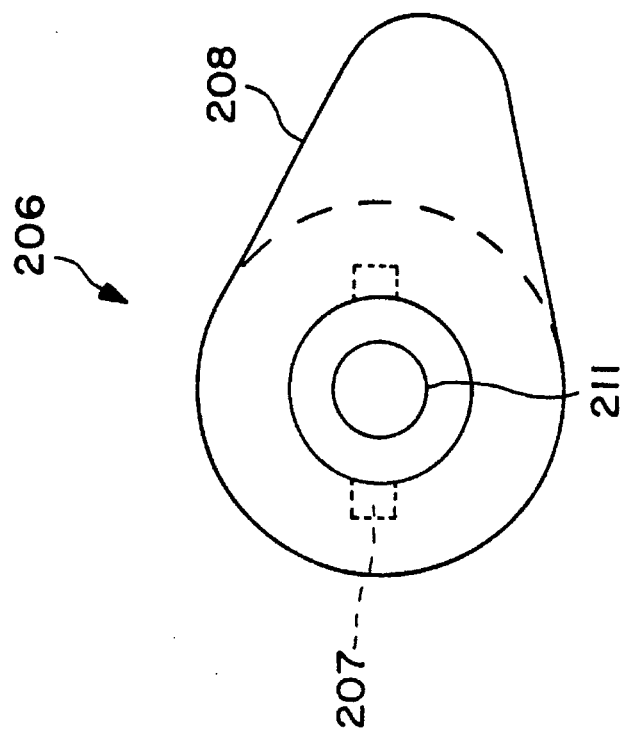
FIG. 4B shows a perspective view of the meatal plate of the urethral plug assembly of the third embodiment.
Figure 4A:
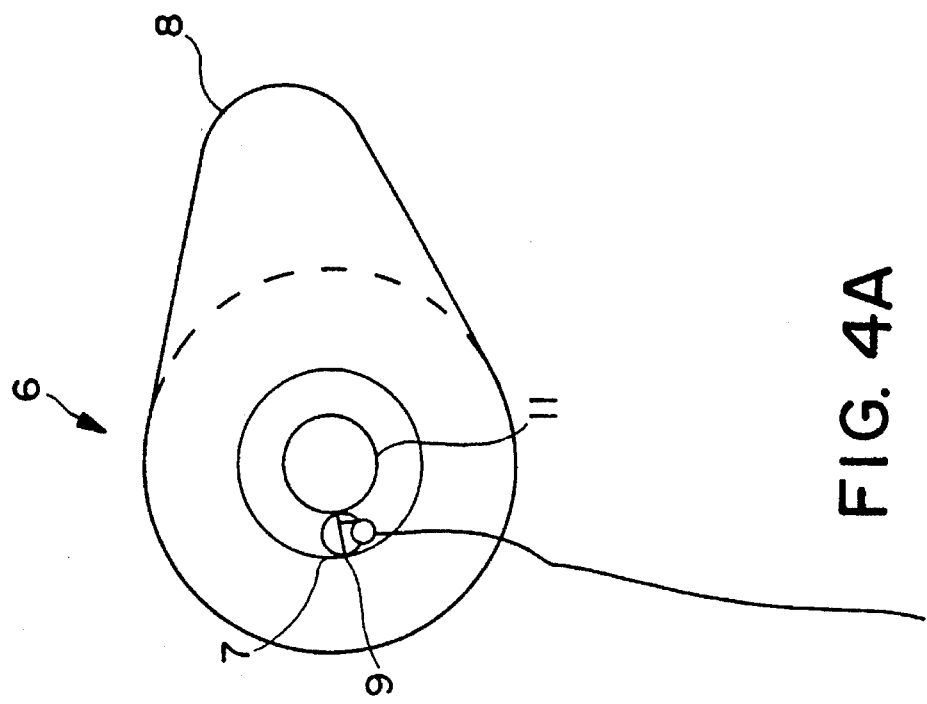
FIG. 4A shows a perspective view of the meatal plate of the urethral plug assembly of the first and second embodiments.

FIG. 4A shows a perspective view of the meatal plate 6, which is the same as a meatal plate 106 in the embodiment shown in FIGS. 2A and 2B, respectively. A portion of the meatal plate 6 is extended so as to form a tab 8 which may be grasped by the wearer for ease of removal. The meatal plate 6 additionally has a ball retention socket 7 and slit 9 formed therein, which, as will be further described, aids in maintaining the plug's expanded configuration during wear. The meatal plate 6 also has an opening 11 therein, lying within the plane of the opening of the outer tube 2.

Referring again to FIG. 1A, enclosed within the tube 2 is a support rod 12, which may be a hollow or a solid member. The support rod 12 has a bulb 14 at one end thereof, abutting the proximal end of the tube 2. The bulb 14 functions to hold the support rod 12 within the tube 2. The support rod 12 has a cord 16 attached at its end opposite the bulb 14, which extends through the tube 2 and beyond the meatal plate 6, thus ensuring that a wearer will always be able to reach the cord 16. On the cord 16 there is preferably formed a knot 18. Although the knot 18 has been used, the attachment of any member having a diameter greater than ball retention socket 7 would suffice. The support rod 12 is preferably stainless steel, the outer tube 2 is preferably formed of a biocompatible thermoplastic material and the balloon 4 is preferably a biocompatible thermoplastic elastomer, such as that sold under the trademark KRATON. However, any biocompatible material may be used for each of the aforementioned elements, as the invention is not to be limited to those named above. Line A—A represents the cross sectional view of the tube 2, which will be discussed further with reference to FIGS. 5A and 5B.

A user inserts the plug assembly 10 while it is in the configuration shown in FIG. 1A. Once the plug assembly 10 has been inserted and the meatal plate 6 abuts the meatus urinarius, the plug assembly 10 may be deployed by the wearer, upon which it achieves an expanded configuration, as set forth in FIG. 1B. To deploy, the wearer pulls on the cord 16 depending from the support rod 12. By pulling, a downward force is exerted on the cord 16 in the vertical direction, forcing the support rod 12 to slide downwardly in the tube 2 and exert a compressive force against the proximal end of the outer tube 2. The tube 2 thus expands outwardly in the horizontal direction, causing the balloon 4 to expand until the balloon forms a seal with the wall of the urethra, bladder neck or bladder. The wearer then secures the cord by sliding it through the slit 9 in the ball retention socket 7 located on the meatal plate 6. This causes the knot 18 to act as a stop, as the knot 18 rests within the socket 7, thereby preventing the tube 2 from returning to its contracted state (FIG. 1A). The plug assembly 10 in an expanded form (FIG. 1B) functions to retain and block the flow of urine. When the wearer wishes to remove the plug assembly, a simple tug on the cord 16 in a direction away from the socket 7 will cause the knot 18 to be released therefrom, thus causing the tube 2 to retract. The tube 2 thereby returns to its original diameter prior to insertion, making plug removal a comfortable task. Thus, the tube 2 and balloon 4 cooperatively provide an expandable housing and the plug includes means for mechanically expanding the housing and selectively returning the housing to its non-expanded condition.

FIG. 2A shows a second embodiment of the urethral plug assembly 110 in its contracted configuration. Tube 102 comprises a flexible braided mesh 103. Attached on the periphery thereof either by thermal bonding, laminating or other means, is a sealing membrane, or balloon, 104 which is adapted to rest against the tube 102. Enclosed within the tube 102 is a support rod 112, which may be a hollow or a solid member. The support rod has a bulb 114 at one end thereof, fixed to the proximal end of the tube 102. The bulb 114 functions to secure the support rod 112 within the tube 102. The support rod 112 has a cord 116 attached at its end opposite the bulb 114, which extends through the tube 102 and beyond the meatal plate 106, thus ensuring that a wearer will always be able to reach the cord 116. The cord 116 preferably has formed therein a knot 118. Although a knot 118 has been used, the attachment of any member having a diameter greater than ball retention socket 107 would suffice. The support rod 112 is preferably stainless steel, the outer tube 102 is preferably formed of a biocompatible thermoplastic material and the balloon 104 is preferably a biocompatible thermoplastic elastomer, such as that sold under the trademark KRATON. However, any biocompatible material may be used for each of the aforementioned elements, as the invention is not to be limited to those named above. Line A—A represents the cross sectional view of the tube 102, which will be discussed further with reference to FIGS. 5A and 5B.

The user inserts the plug assembly 110 while it is in the configuration shown in FIG. 2A. Once the plug assembly has been inserted and the meatal plate 106 abuts the orifice of the urethra, the plug assembly is deployed by the wearer, upon which it achieves the expanded configuration 120 as set forth in FIG. 2B. To deploy, the wearer pulls down on the cord 116, in a direction opposite the direction of initial insertion of the device. Thus, a compressive force is exerted in the vertical direction by the cord 116 on the bulb 114, which is transmitted from the bulb 114 to the tube 102. This force causes the braided mesh 103 to expand outwardly in the horizontal direction. The expansion of the braided mesh forms an oval projection, which projection causes the balloon 104 to expand therewith. The wearer then secures the cord 116 by sliding it through the slit (not shown, see FIG. 4A, element 9 ) in the ball retention socket 107 in the meatal plate 106. This causes the knot 118 to act as a stop, as the knot is brought to rest within the socket 107, thereby preventing the braided mesh 103 from returning to its contracted state 110 (FIG. 2A). The balloon thus retains its seal with the urethral, bladder neck or bladder wall and functions to block the flow of urine.

When the wearer wishes to remove the plug assembly, a simple tug on the cord 116 in a direction away from the socket 107 will cause the knot 118 to be released therefrom, thus causing the braided mesh 103 to retract. The tube 102 thereby returns to its original diameter prior to insertion, making plug removal a comfortable task.

FIG. 3A shows the plug assembly 210 of the third embodiment of the present invention in its contracted state. An outer tube 202 has a plurality of elongated apertures 201 are formed therein. Line A—A represents the cross sectional view of the outer tube 202 which will be discussed further with reference to FIGS. 5A and 5B. Attached to the periphery of the outer tube 202, is a sealing membrane, or balloon 204 which is its preinsertion configuration (FIG. 3A), is adapted to rest against the outer tube 202. At the proximal end of the outer tube 202 is an end cap 214. At the distal end of the outer tube 202 is a meatal plate 206 which has a thickness sufficient to prevent compression thereof while the plug assembly is worn. As shown in a perspective view in FIG. 4B, the meatal plate 206 has a tab 208 and a a groove 207 within its upper portion, which acts as a retaining means, to be described in further detail below. The meatal plate 206 also has an opening 211 therein, lying within the plane of the opening of the outer tube 202, through which an inner tube 212 passes.

Referring again to FIG. 3A, inner tube 212 fits within the outer tube 202, and is preferably longer than the outer tube 202. The inner tube 212, has a plurality of cuts 213 defining a plurality of elongated segments 215 therein. The inner tube 212 is made from a biocompatible material having a property of compressibility. The inner tube 212 further has a flange 218 at its distal end which aids in securing the inner tube 212 within the outer tube 202 after deployment. The inner tube 212 has a cord 216 attached to its bottom end, which aids in the removal of the plug assembly 210.

The user inserts the plug assembly 210 while it is in the configuration shown in FIG. 3A. Once the plug assembly has been inserted and the meatal plate 206 abuts the meatus urinarius, the plug assembly 210 may be deployed by the wearer, whereupon it achieves the expanded configuration set forth in FIG. 3B. To deploy, the wearer pushes the inner tube 212 into the outer tube 202, thus causing the proximal end of the inner tube 212 to abut the end cap 214 of the outer tube 202. The wearer continues to push in the vertical direction until the elongated segments 215 of the inner tube 212 expand in the horizontal direction. The elongated segments 215, thus flare-out, until each elongated segment 215 pops through one of the elongated apertures 201 in the outer tube. Upon popping through the apertures 201, the elongated segments 215 cause the balloon 204 to expand. The wearer continues to push until the flange 218 of the inner tube 212 is received in the groove 207 of the outer tube 202, whereupon the two members form a snap-fit thereby locking the elongated segments 215 in a flared configuration.

The balloon 204, having expanded with the flaring of the elongated segments 215, thus forms a seal with the urethral, bladder neck or bladder wall, and thus functions to retain the device and block the flow of urine. When the wearer wishes to remove the plug assembly 210, a simple tug on the cord 216 breaks the snap fit connection between the flange 218 and the groove 207, thereby releasing the flange. This releasing action will cause the elongated segments 215 of the inner tube 212 to retract as the distal end of the inner tube 212 is pulled down and away from abutment with the end cap 214. Thus, the elongated segments 215 will again lie flush within the outer tube, as shown in FIG. 3A, making removal of the plug assembly a comfortable and easy procedure.

Figure 5B:
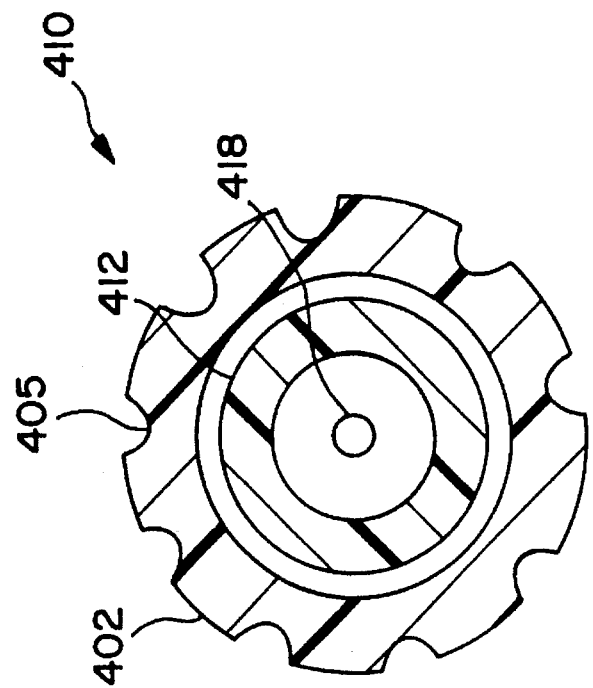
FIG. 5B is similar to FIG. 5A, but shows a cross sectional view of an alternative embodiment of the urethral plug assembly.
Figure 5A:
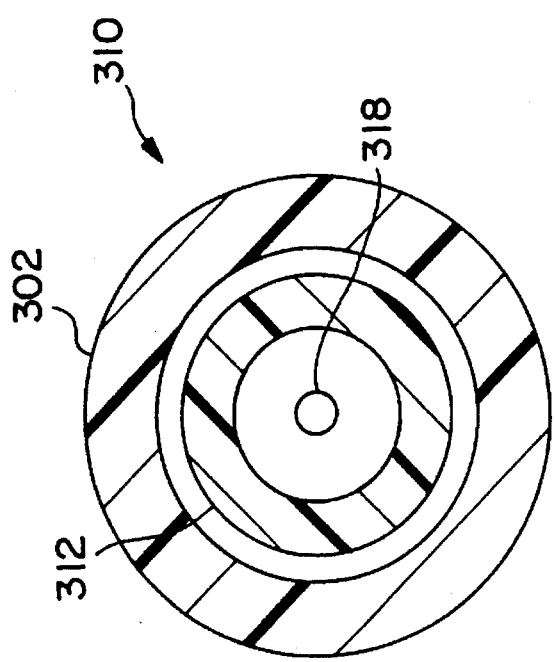
FIG. 5A shows an cross sectional view of the urethral plug assembly, taken along line A—A of FIG. 1A.

FIG. 5A shows a cross sectional view of the urethral plug assembly 310 along line A—A of the preferred embodiments set forth above. Tube 302, representative of tubes 2, 102 and 202, respectively, is of constant diameter. As described above, support rod 312 may be solid or hollow and lies within tube 302. Knot 318 is also shown as it applies to the first two embodiments. FIG. 5B shows an alternative embodiment of the urethral plug assembly 410, along line A—A, of the cross section of tubes 2, 102 and 202 respectively. As shown, the diameter of tube 402 is not constant but variant as shown by the curved indentations 405 on the periphery. The indentations 405 provide enhanced surface area by which the plug assembly may more readily adapt to the urethral, bladder neck or bladder wall. Such enhanced sealing ability of the plug assembly, provides a better fit for the wearer. As described above, support rod 412 may be solid or hollow and lies within tube 402. Knot 418 is also shown as it applies to the first two embodiments.

The instant invention provides a novel plug assembly which may be comfortably worn in the urethra. The ability of the plug to expand from a smaller to a larger diameter for operation in the urethra, and return to its smaller diameter for removal, makes the plug easily manipulable by the wearer. Additionally, the construction of the instant invention provides enhanced sealing of the plug with the urethra, bladder neck or bladder, making leakage of urine unlikely. This construction additionally provides a device which does not require an airtight seal, as expansion is carried out by members which do not rely on internal fluid for expansion, but rather a mechanical means. Moreover, the plug assembly, being equipped with a meatal plate, permits the plug to remain safely anchored at the meatus, thereby preventing migration into the bladder. Lastly, the plug assembly is easily removed for bladder evacuation.

While the invention has been particularly shown and described with reference to the aforementioned embodiments, it will be understood by those skilled in the art, that various changes in form and detail may be made therein without departing from the spirit and scope of the invention. Thus, any modification of the shape, configuration and composition of the elements comprising the invention is within the scope of the present invention.

I hereby claim:

1. A remove-to-void plug assembly for use in the urethra to control urinary incontinence, comprising:

a housing adapted to be inserted into the natural urethral opening of a wearer, a solid element coupled with said housing, which solid element directly impacts on said housing so as to mechanically change the shape of said housing causing at least a portion of said housing to expand outwardly to contact the walls of the urethra, bladder neck or bladder, wherein the mechanical change in shape is effectuated by the wearer after insertion of said housing into the natural urethral opening, said at least a portion of said housing thereby forming a seal with the walls to block the flow of urine without the formation of a passageway through said housing, and means for reversing the change in shape of said housing to return said housing to its non-expanded state, thereby enabling the wearer to remove said housing from the natural urethra opening and effect bladder evacuation.

2. The plug assembly according to claim 1, said means for reversing the changing of the shape of said housing being integrally connected to the plug assembly.

3. The plug assembly according to claim 1, said housing further comprising an expandable tube having a membrane mounted thereon.

4. The plug assembly according to claim 1, said solid element for changing the shape of said housing comprising a rod positioned within said housing and movable within said housing to cause said changing of the shape of said housing.

5. The plug assembly according to claim 4, said rod having a bulk, fixed thereon, whereby movement of said rod causes said bulb to exert a force on said housing causing said changing of the shape of said housing.

6. The plug assembly of claim 4, said means for reversing the changing of the shape of said housing comprising a cord fixed to said rod and extending from said housing, whereby manipulation of said cord causes said movement of said rod in said housing.

7. The plug assembly of claim 6, wherein said assembly further comprises means for securing said housing in an expanded state.

8. The plug assembly of claim 7, wherein said means for securing said housing in said expanded state comprises means for retaining a portion of said cord in a non-movable state.

9. The plug assembly of claim 8, said means for retaining a portion of said cord comprising a socket.

10. The plug assembly of claim 9, said portion of said cord comprising a knot.

11. The plug assembly of claim 1 wherein said housing has a groove therein, and said solid element for mechanically changing the shape of said housing comprises a rod having a flange disposed thereon, said groove adapted to receive said flange so as to maintain the housing in an expanded state.

12. The plug assembly of claim 1, said housing further comprising a meatal plate.

13. The plug assembly of claim 12, said meatal plate further comprising a tab extending from a distal end of said housing, lying substantially normal to said housing.

14. The plug assembly of claim 1, said housing comprising a braided mesh.

15. The plug assembly of claim 1, said housing having curved indentations on the periphery thereof.

16. The plug assembly of claim 1, said housing comprising an outer tube having a plurality of apertures therein.

17. The plug assembly of claim 16, said solid element for mechanically changing the shape of said housing comprising an inner tube having a plurality of elongated segments.

18. A plug assembly adapted to be inserted in the urethra for controlling urinary incontinence, comprising;

a housing having a plurality of apertures therein, a member having a plurality of expandable segments, said member cooperating with said housing such that said segments project through said apertures when a force is applied to said member.

19. The plug assembly of claim 18, said housing further comprising means for maintaining said segments in a projected configuration.

20. The plug assembly of claim 19, said means for maintaining said segments in said projected configuration comprising a groove in said housing and a flange on said member adapted to form a snap-fit with said groove.

21. The plug assembly of claim 20, said member further comprising a flange adapted to form a snap-fit with said groove.

22. The plug assembly of claim 18, said housing having curved indentations on the periphery thereof.

23. The plug assembly of claim 18, said housing further comprising a meatal plate.

24. The plug assembly of claim 23, said meatal plate having a thickness sufficient to withstand compression by the urethra.

25. The plug assembly of claim 18, said housing further comprising a membrane.

26. The plug assembly of claim 18, further comprising means for reversing the projection of said segments.

27. The plug assembly of claim 26, wherein said means for reversing the expansion comprises a cord.

28. A method for controlling urinary incontinence comprising:

a) providing a remove-to-void urethral plug assembly having an expandable housing and a solid element for mechanically expanding said housing, b) inserting said plug assembly into the natural opening of the urethra, c) exerting a force on said solid element for mechanically expanding said housing, wherein the force exerted is imposed by a wearer of the urethral plug assembly, d) mechanically expanding said housing via the force on said solid element impacting on said housing, until the flow of urine is blocked, e) reversing the mechanically expanded housing to return said housing to its non-expanded state, whereby said reversing is effectuated by the wearer, and f) removing the plug assembly from the natural opening of the urethra to allow the wearer to void the bladder.

29. The method of claim 28, further comprising;

expanding a sealing membrane while mechanically expanding said housing, whereby said solid element enables said sealing membrane to remain expanded notwithstanding a rupture of said sealing membrane.

30. The method of claim 28, further comprising;

manipulating a member coupled to said means for mechanically expanding said housing, for retraction of said expandable housing and removal of said plug assembly.

31. A method for controlling urinary incontinence comprising:

a) providing a urethral plug assembly comprising a housing having apertures therein, and a solid element for mechanically expanding segments within said housing, b) inserting said plug assembly into the natural opening of the urethra, and c) exerting a force on said solid element for mechanically expanding said segments, so as to mechanically expand said segments through said apertures in said housing until the flow of urine is blocked.

32. The method according to claim 31, further comprising; expanding a sealing membrane while mechanically expanding said segments.

33. The method of claim 31, further comprising: manipulating means for reversing the expansion of said elongated segments for removal of said plug assembly.

34. A plug assembly for use in the urethra to control urinary incontinence comprising:

a housing comprising a member having curved indentations on the periphery thereof to effect improved sealing of said housing with a wall of the urethra, a solid element for changing the shape of said member, means for reversing the changing of the shape of said member.

35. A plug assembly for use in the urethra to control urinary incontinence comprising:

a housing adapted to be inserted into the natural opening of the urethra, including a meatal plate adapted to abut the urethral meatus, having a thickness sufficient to withstand compression by the urethra, a solid element for mechanically changing the shape of said housing, means for reversing the changing of the shape of said housing.

36. The plug assembly of claim 35, said meatal plate having a thickness of at least one millimeter.

37. A plug assembly for use in the urethra to control urinary incontinence, comprising:

a housing adapted to be inserted into the natural urethral opening of a wearer, a solid element for mechanically changing the shape of said housing, comprising a rod positioned within said housing and moveable within said housing to change the shape of said housing, means for reversing the changing of the shape of said housing.

* * * * *